Figure 1:
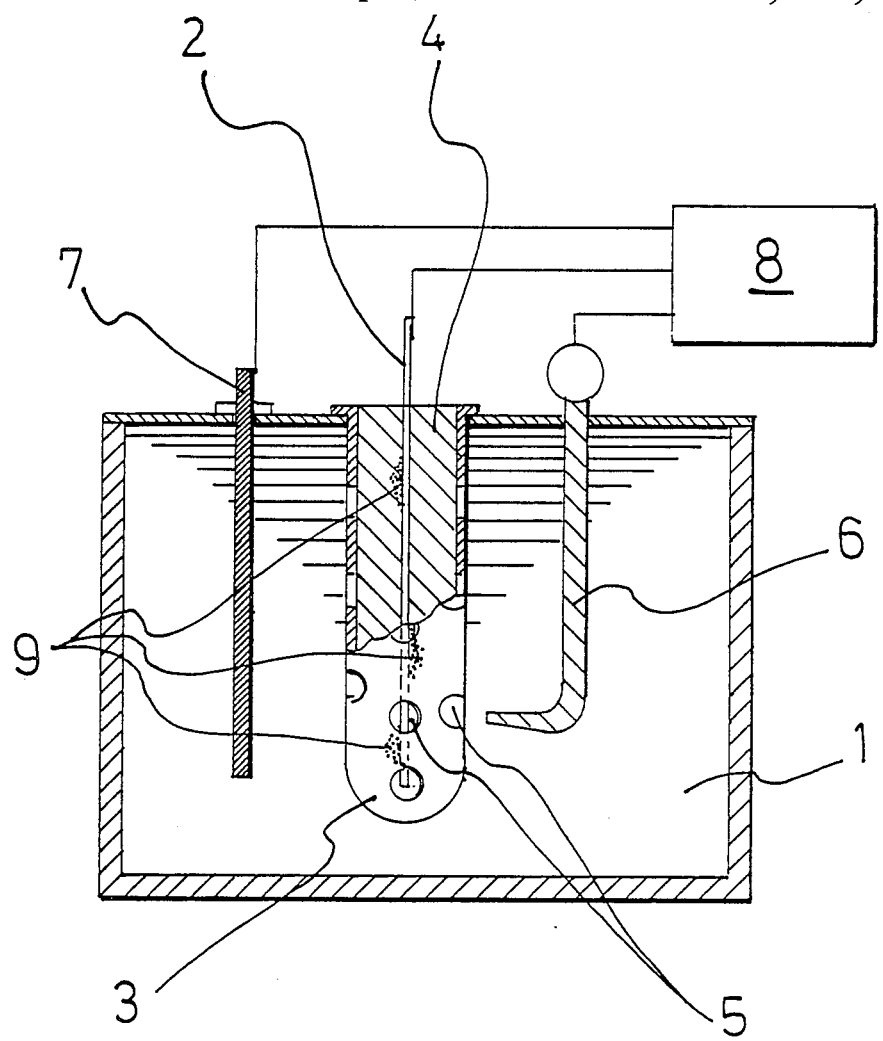

United States Patent [19]

Chambaere

[11] Patent Number: 4,863,571
[45] Date of Patent: Sep. 5, 1989

[54] METHOD OF TESTING FOR CORROSION

[75] Inventor: Daniël Chambaere, Wevelgem, Belgium

[73] Assignee: N.V. Bekaert S.A., Zwevegem, Belgium

[21] Appl. No.: 188,540

[22] Filed: Apr. 29, 1988

[30] Foreign Application Priority Data

May 7, 1987 [BE] Belgium .............................. 8700494

[51] Int. Cl.[4] ........................................... G01N 27/46
[52] U.S. Cl. ..................................... 204/1 T; 204/404
[58] Field of Search ............................... 204/1 C, 404

[56] References Cited

U.S. PATENT DOCUMENTS

| | | | |
|---|---|---|---|
| 3,449,232 | 6/1969 | Bailey | 204/404 |
| 3,549,993 | 12/1970 | Marsh et al. | 324/71.1 |
| 3,878,064 | 4/1975 | Weisstuch et al. | 204/1 C |
| 4,221,651 | 9/1980 | Mansfeld | 204/404 |

*Primary Examiner*—Aaron Weisstuch
*Attorney, Agent, or Firm*—Cushman, Darby & Cushman

[57] ABSTRACT

The invention relates to a method for simulating and determining the corrosion behavior of an electrically conducting element (2) when said element is embedded in a polymer matrix. The corrosion is determined by mounting the element as working electrode (2) in a usual measuring cell (1) for electrochemical corrosion. The element is thereby embedded in a viscous, preferably transparent mass (4) as electrolyte containing selected substances capable of attacking the element (2).

5 Claims, 1 Drawing Sheet

METHOD OF TESTING FOR CORROSION

The invention relates to a method of testing for corrosion. In particular, the invention relates to a method for simulating and determining the corrosion behavior of an electrically conducting element embedded in a polymer matrix such as rubber or synthetic resins.

Rubber is often reinforced with metal elements such as wires, cords, or plates. Metal wires and wire netting or plates are also often protected against corrosion by plastic coating. In addition, metal fiber or metalized fiber are nowadays often incorporated into synthetic resins to increase their electrical conductivity. Polymers are also used to insulate electrical cables. The rubber products thus reinforced (as for instance vehicle tires, pressure hoses, or conveyor belts), plastic coated wires or plates or metal fiber filled resin products will often be subjected to atmospheric corrosion during use. Occasionally, they may also be used in particularly aggressive or corrosive environments. In this case, great care must be taken to avoid corrosion of the elements with a metal surface. For this purpose corrosion inhibitors are often used.

The determination of the corrosion behavior, in particular the rate of corrosion of metals in aggressive environments by electrochemical corrosion tests is known per se. Such tests have for instance been described on pages 43 and 44 in the handbook "Corrosion Basics", published in 1984 by the National Association of Corrosion Engineers—Houston, Tex., U.S.A. According to this commonly used test, the electrically conducting element to be investigated is positioned as a working electrode in a liquid electrolyte and facing a counter or auxiliary electrode. A reference electrode is also introduced into the measuring cell and the corrosion behavior is determined and controlled through a potentiostat connected to the electrodes.

For simulating the corrosion behavior of a conducting element in a polymer matrix, this method has the disadvantage that the rate of diffusion and the mobility of the molecules, atoms, ions, and electrons close to the working electrode in the electrolytic cell are much higher than in the actual corrosion process occurring in the rubber or resin matrix or in the coating surrounding the element. Moreover, convection of the liquid in the measuring cell may dissolve or entrain the corrosion products formed or the (possibly poorly adhering) corrosion inhibitors applied to the element, which would distort the corrosion measurements. Besides, the water concentration in the rubber or resin matrix around the element is always much lower than in an aqueous electrolyte. For rubber, the concentration usually lies between 0.4 and 1.2%.

It is an object of the invention to remedy these shortcomings by surrounding or coating the conducting element, i.e. the working electrode in the measuring cell, with a viscous mass serving as an electrolyte and containing selected compounds that can attack the element. By the use of this viscous mass the mobility of the particles responsible for the corrosion is impaired, as a result of which the corrosion behavior as occurring in actual practice when the element is embedded in a polymer matrix is simulated fairly accurately.

The corrosion test according to the invention also simulates the phenomenon of atmospheric corrosion of a conducting element which is surrounded by a polymer much more accurately than can be achieved by a test in aqueous electrolytes. During atmospheric corrosion a very thin electrolyte film is formed by adsorption on the surface of the conducting element. In this film the mobility of the ions is also much less than when the element is submerged in an aqueous electrolytic cell. Atmospheric corrosion cannot always be avoided and can especially attack the (metal) element during its treatment and handling in one or other manufacturing process or bonding or embedding process involving a polymer matrix.

A transparent gel will preferably be chosen as the viscous mass in order to render the corrosion process more visible.

The conducting element can be surrounded by the viscous mass by introducing the viscous mass into a container made from inert material and by placing the element in the container in such a way that it is completely surrounded by the mass except for one of its ends which remains free to be connected to the potentiostat. The container has a wall that is permeable to liquid. This wall is for instance perforated, thus permitting direct contact and the passage of current between the liquid and the viscous electrolytes through the perforations when the filled container is immersed in the liquid electrolyte bath close to a reference electrode. Under no circumstance shall the element come into direct contact with the liquid in the measuring cell. Provided the viscous mass is sufficiently coherent and adheres sufficiently to the electrode, this electrode can, if so desired, also be removed with its surrounding viscous mass from the container (which may then even have a non-perforated or non-permeable wall) and immersed directly into the liquid electrolyte. In this manner, a maximum contact surface is realized between the liquid and the viscous electrolyte mass.

In the accompanying FIG. 1 a measuring cell according to the invention has been represented schematically.

EXAMPLE

The measuring cell represented in the accompanying drawing comprises the usual bath 1 containing the aqueous electrolyte and a conducting element 2, the corrosion behavior of which is to be investigated, as working electrode and consisting of a brass coated steel wire surrounded by the viscous mass 4 contained in container 3. The container 3 can be a transparent plastic test tube provided with holes 5 in its wall. Preferably, element 2 is positioned as centrally as possible in the volume of the surrounding viscous mass 4. Contact between the liquid and the viscous electrolyte is thus established through the holes 5. Close to the container 3 the usual reference electrode 6 (for instance saturated calomel electrode) is positioned as well as a counter electrode 7, for instance a graphite bar. The three electrodes 2, 6 and 7 are then connected in a suitable manner to the potentiostat 8 from where the electrical corrosion currents and potentials in the measuring cell are controlled and recorded. The corrosion behavior may, if so desired, be processed numerically using a computer.

It is possible to study the corrosivity of different environments, in particular with different anions such as chloride, sulphate, nitrate or hydroxy ions. Then the liquid electrolyte will contain a suitable salt (KCl, $K_2SO_4$, etc.) and these corrosion promoters will also be present in the viscous electrolyte surrounding the working electrode 2. The viscous mass can for instance contain gelatine or agar-agar or agarose. An agar-agar gel can for example be prepared as follows:

An aqueous solution is prepared containing for instance 3% by weight of agar-agar and 0.05 mole per liter of KCl or $K_2SO_4$. This solution is heated and transferred into the test tube 3, the holes 5 of which (when present) have been temporarily closed. After cooling, the working electrode 2 to be investigated is introduced into the setting gel. After connecting the electrodes 2, 6, and 7 to the potentiostat, the usual electrochemical tests such as the determination of polarization resistances, Tafel diagrams, potentiodynamic data and cyclic polarization can be carried out in a reproducible manner.

The material going into solution from the working electrode, or in other words the corrosion products 9, accumulate in the gel in the neighborhood of those parts of the element surface that are corrosion sensitive. If a transparent gel such as for instance agar-agar is used, the progress of the corrosion process can be followed visually. If, for example, a working electrode consisting of a brass coated steel filament is investigated, brown spots may appear in the gel when iron is dissolved, and greenish spots when copper dissolves. This corrosion may indicate indirectly on which areas the surface condition of the element deviates from the remainder of the surface, for example as a result of surface damage.

In this context it can also be mentioned that embedding a corrosion sensitive element in a viscous, transparent electrolyte mass may also provide an early idea of how corrosion may proceed in actual practice when the element is surrounded by a polymer matrix or as a result of attack by atmosphere and/or at elevated temperatures.

The test for corrosion according to the invention is also useful to determine the efficiency of certain corrosion inhibitors in preselected corrosive environments. In such instances, the element is introduced into the viscous electrolyte after having been coated with this corrosion inhibitor.

I claim:

1. A method of simulating and determining the corrosion behavior of an electrical conducting element when said element is embedded in a polymer matrix, comprising the steps of:
   (i) providing an electrochemical corrosion measuring cell having as a working electrode said element;
   (ii) placing said element in said cell, said element being surrounded by an electrolyte, which electrolyte is a viscous mass;
   (iii) introducing into said viscous mass at least one substance capable of causing corrosion of said element; and
   (iv) electrochemically determining the corrosive effect of said substance on said element.

2. A method according to claim 1 wherein the viscous mass is a transparent gel.

3. A method according to claim 1 wherein said element and said surrounding viscous mass are introduced into a liquid electrolyte in said measuring cell in the vicinity of a reference electrode whereby direct contact is established between said liquid electrolyte and the viscous mass.

4. A method according to claim 1 wherein the viscous mass and the working electrode are present in a container having a liquid permeable wall.

5. A method according to claim 1 wherein the working electrode is pretreated with a corrosion inhibitor.

* * * * *